(12) United States Patent
Wynkoop

(10) Patent No.: US 10,470,840 B2
(45) Date of Patent: Nov. 12, 2019

(54) SURGICAL SUCTION CLEARING DEVICE

(71) Applicant: Aaron Wynkoop, Flint, MI (US)

(72) Inventor: Aaron Wynkoop, Flint, MI (US)

(*) Notice: Subject to any disclaimer, the term of this patent is extended or adjusted under 35 U.S.C. 154(b) by 456 days.

(21) Appl. No.: 15/393,790

(22) Filed: Dec. 29, 2016

(65) Prior Publication Data

US 2018/0185115 A1 Jul. 5, 2018

(51) Int. Cl.
*A61B 90/70* (2016.01)
*A61M 1/00* (2006.01)
*B05B 15/522* (2018.01)
*B05B 15/55* (2018.01)

(52) U.S. Cl.
CPC .............. *A61B 90/70* (2016.02); *A61M 1/008* (2013.01); *B05B 15/55* (2018.02); *A61B 2090/701* (2016.02); *A61M 2209/10* (2013.01); *B05B 15/5223* (2018.02)

(58) Field of Classification Search
CPC .. A61B 90/70; A61B 2090/701; A61M 1/008; A61M 2209/10; B05B 15/5223; B05B 15/55
USPC .................................. 134/6, 8, 22.11, 166 R
See application file for complete search history.

(56) References Cited

U.S. PATENT DOCUMENTS

| 4,361,926 A | 12/1982 | Brush et al. |
| 5,003,657 A | 4/1991 | Boiteau et al. |
| 5,011,488 A | 4/1991 | Ginsburg |
| 6,183,450 B1 | 2/2001 | Lois |
| 7,833,155 B2 | 11/2010 | Torii |
| 8,157,919 B2 | 4/2012 | Vazales et al. |
| 8,726,453 B2 | 5/2014 | Berry et al. |
| 8,986,285 B2 | 3/2015 | Salehi et al. |
| 9,131,988 B2 | 9/2015 | Bagwell et al. |
| 9,352,122 B2 | 5/2016 | Mulvihill et al. |
| 2007/0204890 A1* | 9/2007 | Torii ................... A61B 1/00091 134/198 |
| 2007/0295776 A1 | 12/2007 | Whelan |
| 2012/0000487 A1 | 1/2012 | Esquenet et al. |
| 2012/0117740 A1 | 5/2012 | Berry et al. |
| 2014/0215736 A1 | 8/2014 | Gomez et al. |
| 2014/0243883 A1 | 8/2014 | Tsukashima et al. |
| 2014/0352724 A1 | 12/2014 | Meyer |

FOREIGN PATENT DOCUMENTS

WO 2015138658 A3 9/2015

* cited by examiner

*Primary Examiner* — Levon J Shahinian
(74) *Attorney, Agent, or Firm* — The Webb Law Firm

(57) ABSTRACT

An apparatus for unclogging a surgical-suction device (21) comprising a base (22) that defines at least one hole (26). A stylet (28) extends perpendicularly from the center of the base (22) along an axis (A) for receiving the surgical-suction device (21). The stylet (28) defines an exterior and an internal chamber (32) that communicates with the hole (26) in the base (22). The stylet (28) defines at least one aperture (40) in fluid communication between the chamber (32) and the exterior of the stylet (28) for communicating with the surgical-suction device (21). A valve (60) having an open position (FIG. 1) for allowing fluid to flow through the hole (26) of the base (22) and the aperture (40) in the stylet (28) and a closed position (FIG. 2) for preventing fluid to flow through the hole (26) of the base (22) and the aperture (40) in the stylet (28).

19 Claims, 3 Drawing Sheets

US 10,470,840 B2

SURGICAL SUCTION CLEARING DEVICE

BACKGROUND OF THE INVENTION

1. Field of the Invention

An apparatus for unclogging a surgical-suction device useful during medical operations.

2. Description of the Prior Art

Apparatuses of the type to which the subject invention pertains are used for unclogging a surgical-suction device particularly during a medical operation requiring the removal of blood or other fluids. Such an assembly is illustrated in U.S. Pat. No. 8,726,453 to Berry et al., wherein a base extends to a peripheral edge and defines at least one hole. A stylet extends perpendicularly from the center of the base along an axis to a terminal end for receiving the surgical-suction device. The stylet defines an exterior and an internal chamber communicating with the hole in the base and extending towards the terminal end. Another such assembly is illustrated in U.S. patent application Ser. No. 12/948,642 to Berry et al., wherein the stylet defines at least one aperture in fluid communication between the chamber and the exterior of the stylet for communicating with the surgical-suction device.

SUMMARY OF THE INVENTION

The invention provides for such apparatuses including a valve having an open position for allowing fluid to flow through the hole of the base and the aperture in the stylet and a closed position for preventing fluid to flow through the hole of the base and the aperture in the stylet.

Advantages of the Invention

The invention in its broadest aspect provides for increased versatilely and mobility. The valve can allow or prevent fluid flow through the hole in the base and the aperture in the stylet.

BRIEF DESCRIPTION OF THE DRAWINGS

Other advantages of the present invention will be readily appreciated, as the same becomes better understood by reference to the following detailed description when considered in connection with the accompanying drawings wherein.

DESCRIPTION OF THE ENABLING EMBODIMENT

Figure 1:
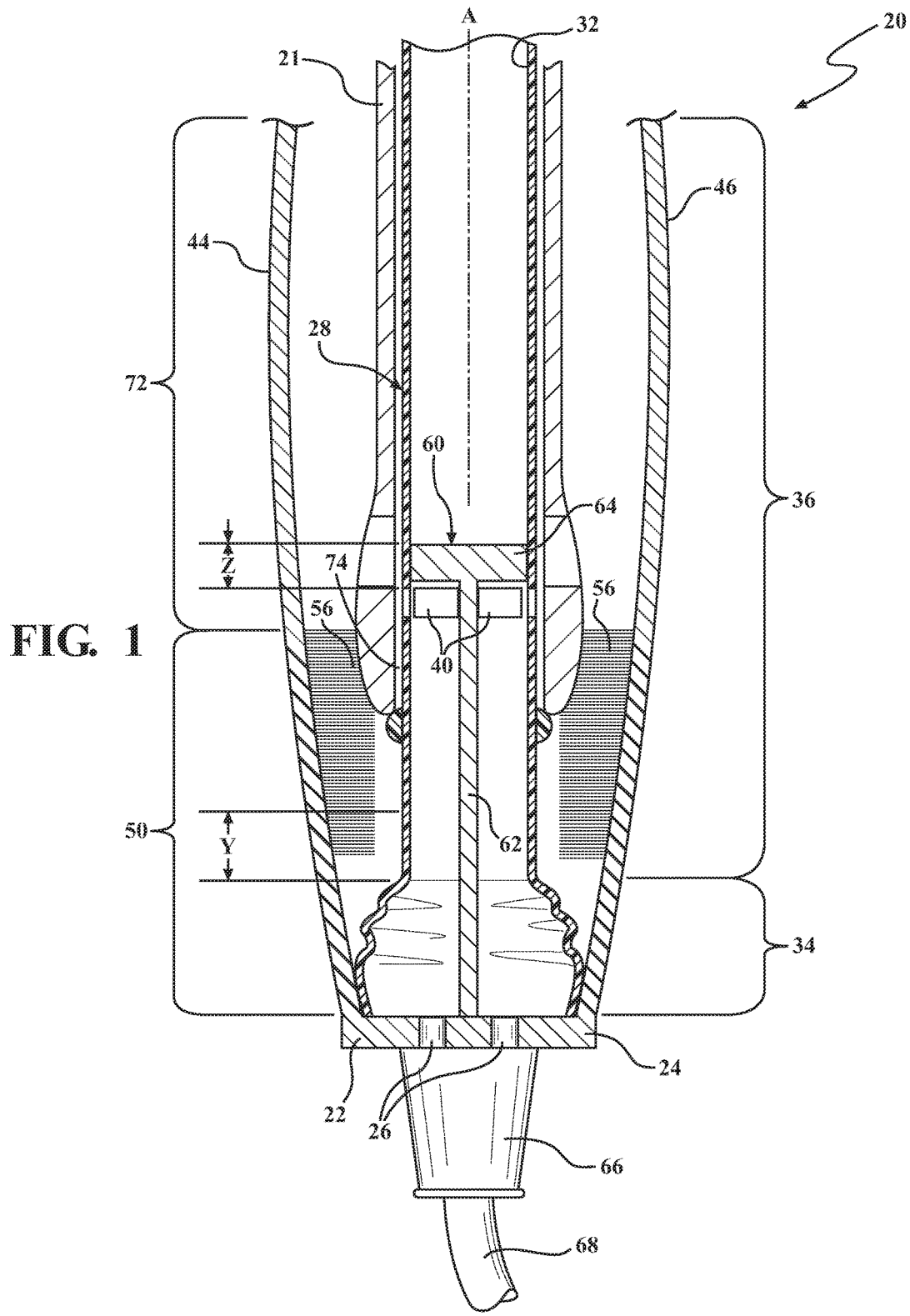
FIG. 1 is view of the valve in the closed position in a fragmentary cross-section.

Referring to the Figures, wherein like numerals indicate corresponding parts throughout the several views, an apparatus (20) for unclogging a surgical-suction device (21) constructed in accordance with the subject invention is generally shown in FIG. 1.

The apparatus includes a base (22) having a circular shape extending to a peripheral edge (24). The base (22) defines at least one hole (26) that extends through the base (22). A stylet (28) extends perpendicularly from the center of the base (22) along an axis (A) to a terminal end (30) for receiving the surgical-suction device (21). The stylet (28) defines an exterior and an internal chamber (32) communicating with the hole (26) of the base (22) and extending towards the terminal end (30) of the stylet (28). The stylet (28) defines at least one aperture (40) in fluid communication between the chamber (32) and the exterior of the stylet (28) for communicating with the surgical-suction device (21).

Figure 2:
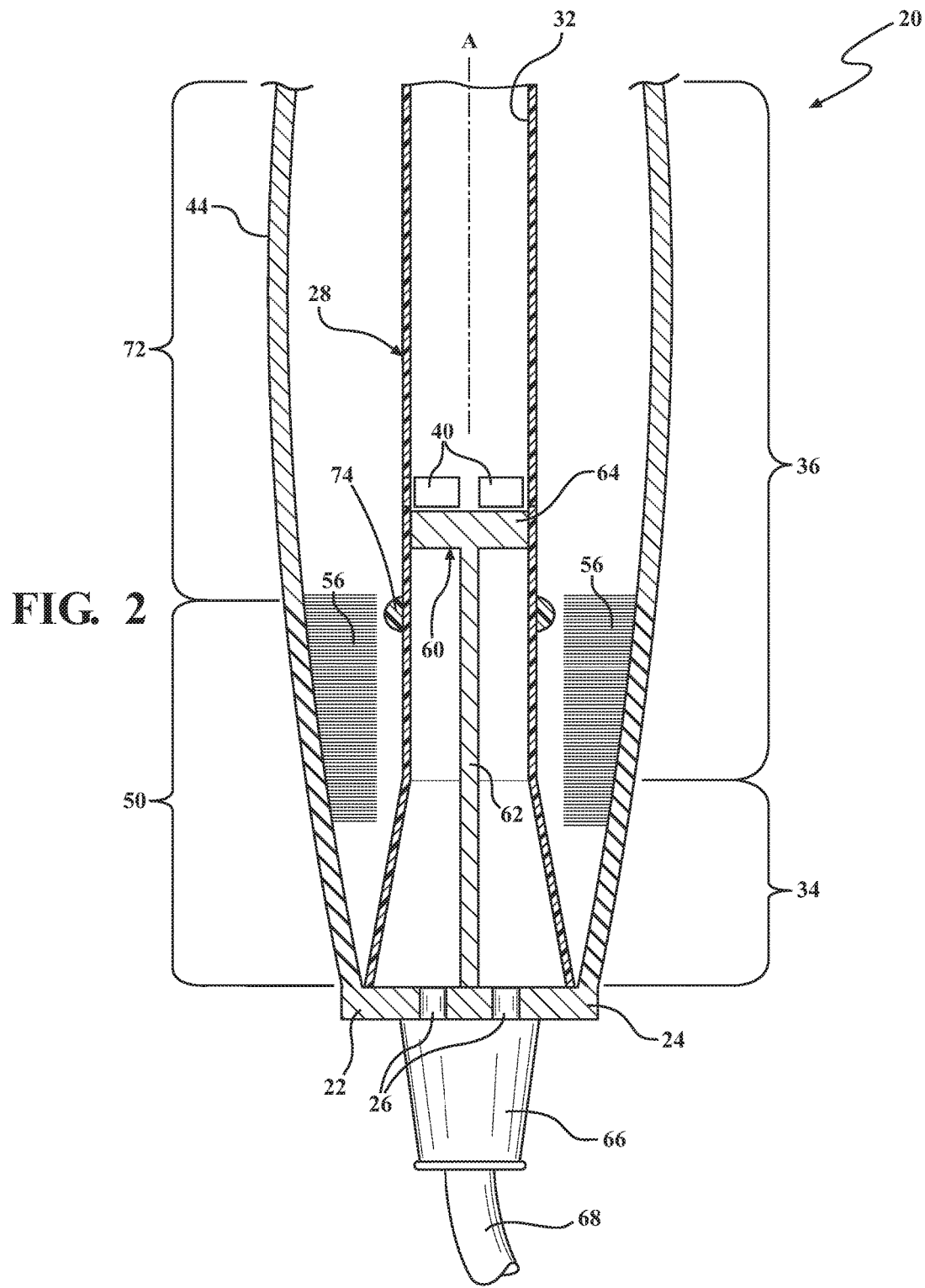
FIG. 2 is view of the valve in the open position in a fragmentary cross-section.
Figure 3:
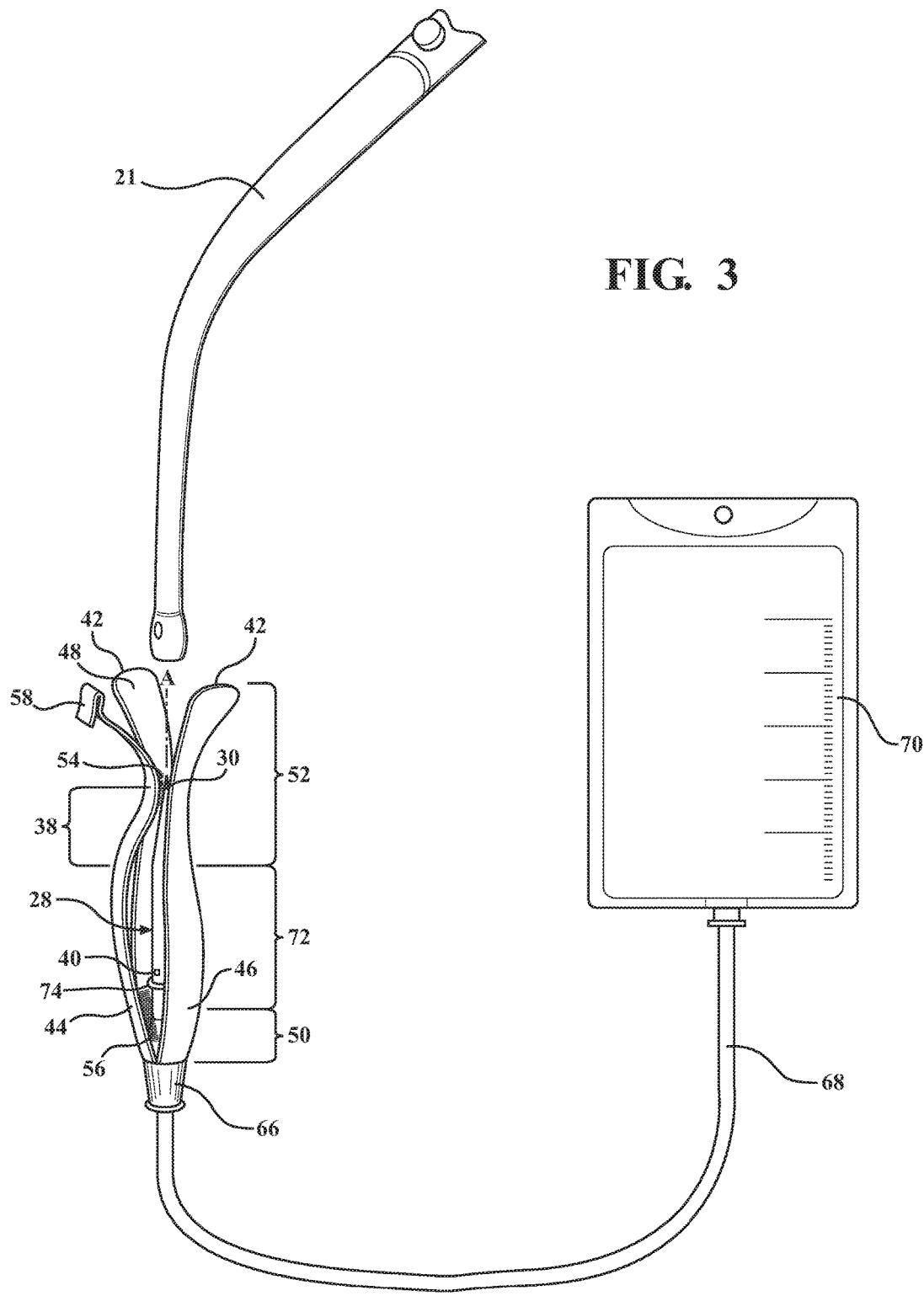
FIG. 3 is a side view of the apparatus.

The stylet (28) includes an actuator (34) for blocking and sealing the aperture (40) in the stylet (28) from the hole (26) in the base (22) in the closed position (FIG. 1) and unblocking and unsealing the aperture (40) in the stylet (28) from the hole (26) in the base (22) in the open position (FIG. 2). The actuator (34) includes a compressible section (34) of the stylet (28) adjacent to the base (22) and covering the hole (26) in the base (22). The compressible section (34) comprises flexible material having axial flexibility for compacting the compressible section (34) a first axial distance (Y).

The stylet (28) includes a straight section (36) that has a cylindrical shape next to the compressible section (34). The stylet (28) further includes an end section (38) extending and tapering from the straight section (36) to the terminal end (30). The end section (38) comprises flexible material having flexibility for bending to receive surgical-suction devices (21) of various sizes and shapes. As it is well understood in the art, surgical-suction devices (21) can come in a multitude of both size and shape.

A plurality of arms (44, 46, 48) extends perpendicularly from the peripheral edge (24) of the base (22) about the axis (A) to arm ends (42). Each arm (44, 46, 48) is spaced further from the base (22) than the terminal end (30) of the stylet (28). In addition, each of the arms (44, 46, 48) have an accordion section (50) that is axially and radially flexible adjacent to the base (22) for compressing each of the plurality of arms (44, 46, 48) against the base (22). The accordion section (50) can comprise different material, e.g., rubber, or can have grooved sides to facilitate the axial and radial flexibility. The arms (44, 46, 48) further define a funnel guide section (52) wherein the arms (44, 46, 48) converge radially inward from the arm ends (42) toward the axis (A) at a position adjacent to the terminal end (30) of the stylet (28). Because the arms (44, 46, 48) extend further from the base (22) than the terminal end (30), the funnel guide section (52) directs and funnels a surgical-suction device (21) along the axis (A) and onto the stylet (28). In addition to funneling the surgical-suction device (21), the funnel guide section (52) grips and holds stationary the surgical-suction device (21) relative to the apparatus (20) providing hands free storage of the surgical-suction device (21) until needed.

Each of the arms (44, 46, 48) supports a plurality of bristles (54, 56) that extends towards the axis (A) for clearing openings on a surgical-suction device (21). As known in the art, many models of surgical-suction devices (21) define a plurality of little openings adjacent to a surgical-suction device end for fluid entry. The bristles (54, 56) include a first group of bristles (54) disposed on the funnel guide section (52) and a second group of bristles (56) disposed on the accordion section (50). As the accordion section (50) is compressed, the second group of bristles (56) changes orientation performing a brush stroke or sweeping motion scrubbing the exterior of the surgical-suction device (21) and also entering the little openings adjacent to the surgical-suction device end. In the preferred embodiment, when the compressible section (34) is compressed all the way, all of the bristles (54, 56) will come in contact with the surgical-suction device (21).

In the preferred embodiment, the plurality of arms (44, 46, 48) includes a first arm (44), a second arm (46), and a third arm (48). However, it should be understood, any number of arms could be used to accomplish the ultimate function. The first arm (44) includes a clip (58) for attachment to the surgical environment. In use, the clip (58) can be attached to an electrocautery quiver, a surgical drape, or any area within convenient reach of the user.

A valve (60) has an open position (FIG. 1) for allowing fluid to flow through the hole (26) of the base (22) and the aperture (40) in the stylet (28). The valve (60) also has a closed position (FIG. 2) for preventing fluid to flow through the hole (26) of the base (22) and the aperture (40) in the stylet (28). In the preferred embodiment, the valve (60) includes a stem (62) that extends from the base (22) into the chamber (32) of the stylet (28) adjacent to the straight section (36). The valve (60) includes a valve head (64) that is disposed on the stem (62) a second axial distance (Z) below the aperture (40) of the stylet (28) when the valve (60) is in the closed position (FIG. 2). At this location, the valve head (64) impermeably seals the chamber (32) in the stylet (28) below the aperture (40) from the exterior of the stylet (28). In this embodiment first axial distance (Y) is at least as large as the second axial distance (Z).

A source of cleaning fluid (66, 68, 70) is used for flowing through the hole (26) in the base (22) when the valve (66) in the open position (FIG. 1). The source of cleaning fluid (66, 68, 70) includes a fluid container (70) containing a clearing solution. In addition, the source of cleaning fluid (66, 68, 70) includes a connector (66). The connector (66) has a conical shape and extends from the base (22) opposite the stylet (28) and is in fluid communication with the hole (26) in the base (22) for connecting and detaching the container (70). The source of cleaning fluid (66, 68, 70) also includes a flexible fluid conduit (68) extending from the container (70) to the connector (66) for conveying fluid and allowing relative movement between the container (70) and the connector (66).

Each of the arms (44, 46, 48) bulge radially outward between the funnel guide section (52) and the base (22) to define a bulbous midsection (72) with greater radial spacing between each of the arms (44, 46, 48) for guiding surgical-suction devices (21) with curved ends between the plurality of arms (44, 46, 48).

A stop (74) is attached to and wraps around the stylet (28) and is disposed between the aperture (40) and the compressible section (34) of the stylet (28). The stop (74) comprises soft cushioning material, e.g., closed cell foam, for occluding the surgical-suction device (21) as it is pressed against the stop (74) thereby quieting suction sounds. The stop (74) can have a cylindrical shape, torus shape, or any other shape that could conceivably occlude the surgical-suction device (21). In addition to quieting the surgical-suction device (21), the stop (74) provides a limit to which the surgical-suction device (21) can be placed onto the stylet (28) before the compressible section (34) of the stylet (28) begins to compress.

In use, the apparatus (20) provides a level of adaptability desired during a medical operation. The flexibility of both the arms (44, 46, 48) and the stylet (28) allow use with surgical-suction devices (21) of any shape or size. If the surgical-suction device (21) has an extreme bend, it silently slides in the radial spacing between arms (44, 46, 48) in the bulbous midsection (72). Because the valve (66) and the source of cleaning fluid (66, 68, 70) can be moved relative to one another, the weight generally associated with a source of cleaning fluid (66, 68, 70) can be spaced from the medical procedure. The user can move freely about an operating room with the apparatus (20) clipped to surgical drapes or an electrocautery quiver without needing to confine to the weight or space required by the source of cleaning fluid (66, 68, 70). The valve (66) ensures that the user has access to the source of cleaning fluid (66, 68, 70) without having to worry about spillage. The connector (66) provides more versatility of movement for the user and makes cleaning the apparatus (20) easier.

Obviously, many modifications and variations of the present invention are possible in light of the above teachings and may be practiced otherwise than as specifically described while within the scope of the appended claims. That which is prior art in the claims precedes the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

What is claimed is:

1. An apparatus for unclogging a surgical-suction device comprising;
   a base extending to a peripheral edge,
   said base defining at least one hole extending through said base,
   a stylet extending perpendicularly from the center of said base along an axis to a terminal end for receiving the surgical-suction device,
   said stylet defining an exterior and an internal chamber communicating with said hole in said base and extending towards said terminal end;
   said stylet defining at least one aperture in fluid communication between said chamber and said exterior of said stylet for communicating with the surgical-suction device;
   a valve having an open position for allowing fluid to flow through said hole of said base and said aperture in said stylet and a closed position for preventing fluid to flow through said hole of said base and said aperture in said stylet; and
   an actuator for blocking and sealing said aperture in said stylet from said hole in said base in said closed position and unblocking and unsealing said aperture in said stylet from said hole in said base in said open position.

2. The apparatus as set forth in claim 1 wherein said actuator includes a compressible section of said stylet comprising flexible material having axial flexibility for compacting said compressible section a first axial distance.

3. The apparatus as set forth in claim 2, wherein said valve includes a stem extending from said base into said chamber of said stylet.

4. The apparatus as set forth in claim 3, wherein said valve includes a valve head disposed on said stem a second axial distance below said aperture in said stylet when said valve is in said closed position for impermeably sealing chamber in said stylet below said aperture from said exterior of said stylet.

5. The apparatus as set forth in claim 4, wherein said first axial distance is at least as large as said second axial distance.

6. The apparatus as set forth in claim 1, further comprising a source of cleaning fluid for flowing through said hole in said base when said valve in said open position.

7. The apparatus as set forth in claim 6, wherein said source comprises a container.

8. The apparatus as set forth in claim 7, wherein said source comprises a connector extending from said base opposite said stylet in fluid communication with said hole in said base for connecting and detaching said container.

9. The apparatus as set forth in claim 8, wherein said source includes comprises a flexible fluid conduit extending from said container to said connector conveying fluid and allowing relative movement between said container and said connector.

10. The apparatus as set forth in claim 1, further comprising a stop attached to and wrapping around said stylet for occluding the surgical-suction device when the surgical-suction device is pressed against said stop for quieting suction sounds.

11. An apparatus for unclogging a surgical-suction device comprising;
 a base extending to a peripheral edge,
 said base defining at least one hole extending through said base,
 a stylet extending perpendicularly from the center of said base along an axis to a terminal end for receiving the surgical-suction device,
 said stylet defining an exterior and an internal chamber communicating with said hole in said base and extending towards said terminal end;
 said stylet defining at least one aperture in fluid communication between said chamber and said exterior of said stylet for communicating with the surgical-suction device;
 a valve having an open position for allowing fluid to flow through said hole of said base and said aperture in said stylet and a closed position for preventing fluid to flow through said hole of said base and said aperture in said stylet; and
 a plurality of arms extending perpendicularly from said base about said axis to arm ends.

12. The apparatus as set forth in claim 11, wherein each of said arm ends are spaced further from said base than said terminal end of said stylet.

13. The apparatus as set forth in claim 11, wherein each of said arms have an accordion section that is axially and radially flexible adjacent to said base for compressing each of said arms against said base.

14. The apparatus as set forth in claim 13, further comprising a funnel guide section defined by said arms converging radially inward from said arm ends toward said axis at a position adjacent to said terminal end of said stylet for funneling a surgical-suction device along said axis and onto said stylet.

15. The apparatus as set forth in claim 14, further comprising a plurality of bristles disposed on each of said arms.

16. The apparatus as set forth in claim 15, wherein said bristles include a first group of bristles disposed on said funnel guide section and a second group of bristles disposed on said accordion section.

17. The apparatus as set forth in claim 16, wherein each of said arms bulge radially outwardly between said arm ends and said base to define a bulbous midsection with greater radial spacing between each of said arms for guiding surgical-suction devices with curved ends.

18. The apparatus as set forth in claim 11, further comprising a clip disposed on a first arm for attachment to a surgical environment.

19. An apparatus for unclogging a surgical-suction device comprising;
 a base having a circular shape extending to a peripheral edge;
 said base defining at least one hole extending through said base;
 a stylet extending perpendicularly from the center of said base along an axis to a terminal end for receiving the surgical-suction device;
 said stylet defining an exterior and an internal chamber communicating with said hole of said base and extending towards said terminal end;
 said stylet defining at least one aperture in fluid communication between said chamber said exterior of said stylet for communicating with the surgical-suction device;
 said stylet comprising an actuator for blocking and sealing said aperture in said sty let from said hole in said base in said closed position and unblocking and unsealing said aperture in said stylet from said hole in said base in said open position;
 said stylet further comprising an end section extending and tapering from said straight section to said terminal end;
 said end section comprising flexible material having flexibility for bending to receive surgical-suction devices of various sizes and shapes;
 a plurality of arms extending perpendicularly from said peripheral edge of said base about said axis to arm ends spaced further from said base than said terminal end of said stylet;
 each of said arms having an accordion section that is axially and radially flexible adjacent to said base for compressing each of said plurality of arms against said base;
 a funnel guide section defined by said arms converging radially inward from said arm ends toward said axis at a position adjacent to said terminal end of said stylet for funneling a surgical-suction device along said axis and onto said stylet;
 each of said arms supporting a plurality of bristles extending towards said axis for clearing openings on a surgical-suction device;
 said bristles including a first group of bristles disposed on said funnel guide section and a second group of bristles disposed on said accordion section;
 the plurality of arms including a first arm and a second arm and a third arm;
 said first arm including a clip for attachment to the surgical environment; and
 a valve having an open position for allowing fluid to flow through said hole of said base and said aperture in said stylet and a closed position for preventing fluid to flow through said hole of said base and said aperture in said stylet,
 wherein said stylet comprises an actuator for blocking and sealing said aperture in said stylet from said hole in said base in said closed position and unblocking and unsealing said aperture in said stylet from said hole in said base in said open position, said actuator comprises a compressible section of said stylet adjacent to said base and said straight section and covering said hole in said base, said compressible section comprises flexible material having axial flexibility for compacting said compressible section a first axial distance, said valve comprises a stem extending from said base into said chamber of said stylet adjacent to said straight section, said valve comprises a valve head disposed on said stem a second axial distance below said aperture of said stylet when said valve is in said closed position for impermeably sealing said chamber in said stylet below said aperture from said exterior of said stylet, said first axial distance is at least as large as said second axial distance, wherein a source of cleaning fluid is provided for flowing through said hole in said base when said valve in said open position, said source comprises including a fluid container containing a clearing solution, said source comprises including a connector having a conical shape and extending from said base opposite said stylet in fluid communication with said hole in said base for connecting and detaching said container, said source comprises a flexible fluid conduit extending from said container to said connector conveying fluid and allowing relative movement between said container and said connector, wherein each of said arms bulges radially outward between said funnel guide section and said base to define a bulbous midsection with greater radial spacing between each of said arms for guiding surgical-suction devices with curved ends between said plurality of arms, and wherein a stop attached to and wrapping around said stylet disposed between said aperture and said compressible section of said stylet comprising soft cushioning material for occluding the surgical-suction device as the surgical-suction device is pressed against said stop for quieting suction sounds.

* * * * *

UNITED STATES PATENT AND TRADEMARK OFFICE
CERTIFICATE OF CORRECTION

PATENT NO. : 10,470,840 B2
APPLICATION NO. : 15/393790
DATED : November 12, 2019
INVENTOR(S) : Aaron Wynkoop Page 1 of 1

It is certified that error appears in the above-identified patent and that said Letters Patent is hereby corrected as shown below:

In the Claims

Column 5, Line 18, Claim 9, after "source" delete "includes"

Column 8, Line 1, Claim 19, after "comprises" delete "including"

Column 8, Line 3, Claim 19, after "comprises" delete "including"

Signed and Sealed this
Eighteenth Day of February, 2020

Andrei Iancu
*Director of the United States Patent and Trademark Office*